US010576069B2

(12) United States Patent
Ghanbari et al.

(10) Patent No.: US 10,576,069 B2
(45) Date of Patent: *Mar. 3, 2020

(54) TREATMENT FOR CHEMOTHERAPY-INDUCED COGNITIVE IMPAIRMENT

(71) Applicant: Panacea Pharmaceutical Inc., Gaithersburg, MD (US)

(72) Inventors: Hossein A. Ghanbari, Potomac, MD (US); Zhi-Gang Jiang, Gaithersburg, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/012,090

(22) Filed: Feb. 1, 2016

(65) Prior Publication Data

US 2016/0235725 A1 Aug. 18, 2016

Related U.S. Application Data

(63) Continuation-in-part of application No. 13/803,482, filed on Mar. 14, 2013, now abandoned.

(51) Int. Cl.
*A61K 31/44* (2006.01)
*A61K 9/127* (2006.01)

(52) U.S. Cl.
CPC .............. *A61K 31/44* (2013.01); *A61K 9/127* (2013.01)

(58) Field of Classification Search
None
See application file for complete search history.

(56) References Cited

U.S. PATENT DOCUMENTS

2006/0160826 A1* 7/2006 Ghanbari ........... A61K 31/4166
514/255.06

OTHER PUBLICATIONS

Miguel López-Lázaro, "Dual role of hydrogen peroxide in cancer: Possible relevance to cancer chemoprevention and therapy," Cancer Letters, vol. 252, Issue 1, pp. 1-8 (2007).*
Amrani et al, "Brain infarction following 5-fluorouracil and cisplatin therapy," Neurology, vol. 51, No. 3, pp. 899-901 (Year: 1998).*
Serrano-Castro et al, "Ischemic stroke following cisplatin and 5-fluorouracil therapy: a transcranial Doppler study," European Neurology, vol. 44, No. 1, pp. 63-64 (Year: 2000).*

* cited by examiner

*Primary Examiner* — Dennis J Parad
(74) *Attorney, Agent, or Firm* — John W. Ryan (57) ABSTRACT

The present invention provides methods and compositions for treating chemotherapy-induced cognitive impairment. One embodiment of the present invention is directed to a method of treating chemotherapy-induced cognitive impairment by administering to a patient in need at least one thiosemicarbazone compound.

21 Claims, 5 Drawing Sheets

TREATMENT FOR CHEMOTHERAPY-INDUCED COGNITIVE IMPAIRMENT

BACKGROUND OF THE INVENTION

Chemotherapy has improved survival rates in patients with many of the common cancers. However, one of the most common complications of chemotherapeutic drugs is toxicity to the central nervous system (CNS), named chemotherapy-induced cognitive impairment, chemotherapy-induced cognitive dysfunction, post-chemotherapy cognitive impairment (PCCI), chemo fog, or chemo brain. Chemo brain can be very frustrating both for those who are living with cancer, and their loved ones who are trying to support them. Chemo brain can seriously affect quality of life and life itself in cancer patients. This toxicity can manifest in many ways, including encephalopathy syndromes and confusional states, seizure activity, headache, cerebrovascular complications and stroke, visual loss, cerebellar dysfunction, and spinal cord damage with myelopathy. There is reliable evidence that, as a result of treatment, a subset of cancer survivors experience cognitive problems that can last for many years after the completion of chemotherapy. These include attention deficits, memory loss, and confused thought processes. Up to 70% of patients report that their cognitive difficulties persist well beyond the duration of treatment. Studies that have measured cognitive function using standardized neuropsychological assessments have found mild to moderate effects of chemotherapy on cognitive performance in 15-50% of the survivors after treatment. Longitudinal studies have shown that, in a subset of survivors, cognitive difficulties can persist for between 1 and 2 years after the completion of chemotherapy. Cross-sectional studies have found cognitive impairments lasting between 4 and 10 years after chemotherapy. Although recent prospective studies show that about 20% of cancer patients experience cognitive dysfunction even before chemotherapy, chemotherapy agents produce significant cognitive impairment in laboratory animals that are free from cancer as well as from other treatment- and diagnosis-related factors. Healthy rodents that are given chemotherapy show increase in cell death in the central nervous system, increase in oxidative stress, increase in microglia activity, suppression of hippocampal neurogenesis, decreases in levels of neurotrophic factors, and decreases in levels of hippocampal catecholamines, as compared to baseline values. The etiology of chemotherapy-induced cognitive impairment is largely unknown, but several candidate mechanisms have been suggested, including oxidative stress, impaired blood-brain barrier (BBB), neuroinflammation, decreased neurogenesis, etc.

Oxidative stress plays a key role in cognitive disorders caused by certain type of anticancer drugs, such as antimetabolites, mitotic inhibitors, topoisomerase inhibitors and paclitaxel etc. These chemotherapeutic agents are not known to rely on oxidative mechanisms for their anticancer effects. Among the antimetabolite drugs, methotrexate (MTX), 5-fluorouracil (5-FU, a widely used chemotherapeutic agent), and cytosine arabinoside are most likely to cause CNS toxicity. 5-FU can cause both acute and delayed neurotoxicity. Acute neurotoxicity manifests as encephalopathy cerebellar syndrome or as seizures. Acute neurotoxicity due to 5-FU is dose-related and generally self-limiting. 5-FU readily crosses the blood-brain barrier and disrupts cell proliferation. Clinically relevant concentrations of 5-FU were toxic for both central nervous system (CNS) progenitor cells and non-dividing oligodendrocytes in vitro and in vivo. Short-term systemic administration of 5-FU caused both acute CNS damage and a syndrome of progressively worsening delayed damage to myelinated tracts of the CNS associated with altered transcriptional regulation in oligodendrocytes and extensive myelin pathology. Functional analysis also provided the first demonstration of delayed effects of chemotherapy on the latency of impulse conduction in the auditory system, offering the possibility of non-invasive analysis of myelin damage associated with cancer treatment. Delayed neurotoxicity has been reported when fluorouracil was given in combination with levamisole; this form of subacute multifocal leukoencephalopathy is immune mediated. Although no report for 5-FU to increase CNS oxidative stress has been found yet, it has been indicated inducing apoptosis in rat cardiocytes through intracellular oxidative stress, increasing oxidative stress in the plasma of liver cancer patients, and decreasing glutathione in bone marrow cells. Another antimetabolite MTX can cross the blood-brain barrier as well. It resulted in an increase of oxidative stress in cerebral spinal fluid and executive dysfunction in MTX-treated patients of pediatric acute lymphoblastic leukemia. A recent observation also indicates that genetic polymorphism for methionine is a potent risk factor for MTX-induced central nervous system toxicity.

Oxidative stress could be a common path for chemotherapy-induced cognitive impairment and neurodegenerative diseases. Oxidative stress can cause single and double DNA strand breaks and is the most frequent cause of DNA damage in neuronal cells. Oxidative damage can occur through exposure to foreign agents or result from an endogenous mechanism. Oxidative damage has been associated with numerous neurodegenerative diseases such as Alzheimer's disease and Parkinson's. Patients displaying mild cognitive impairment exhibit higher levels of oxidative DNA damage in both peripheral leukocytes and the brain. Many chemotherapeutic agents take advantage of the DNA damaging effects of oxidative stress; however, the effects of oxidative stress are not confined to abnormal cells. Evidence of oxidative damage has been seen in peripheral blood lymphocytes in breast cancer patients treated with chemotherapy. In addition, chemotherapy patients displayed decreased DNA repair abilities. Chemotherapy treatment is associated with increased levels of nonprotein bound iron, increased levels of free radicals, and decreased antioxidant capacity, all factors suggested to increase oxidative stress. It is proposed that MTX treatment inhibits protective factors that may prevent radical damage. As a result, poly-unsaturated fatty acid chains within the cell membranes are more susceptible to attack by reactive oxygen species. These initial attacks signal other lipid peroxy radicals to form, triggering a cascade of cell membrane damage.

Currently there are no proven treatments for chemotherapy-induced cognitive impairment. Some efforts have been focused on correcting cognitive deficits rather blocking neurotoxic pathway that was induced with chemotherapeutical drug. These include erythropoietin (a glycoprotein to stimulate the production of red blood cells), methylphenidate (modulating catecholaminergic tone), modafinil (releasing catecholamines, norepinephrine, dopamine and histamine), donepezil (a cholinesterase inhibitor), and fluoxetine (a selective serotonin reuptake inhibitor). In contrast to above, antioxidative treatment would be a promising strategy for the treatment. Consumption of foods high in antioxidants and antioxidant supplementation appear to slow the rate of cognitive decline associated with aging and disease in humans and rodents. Several preclinical studies have shown that antioxidant treatment prevents chemotherapy-induced oxidative stress and cognitive deficits when administered prior to and during chemotherapy. For example, systemic treatment in healthy mice with γ-glutamyl cysteine ethyl ester prior to doxorubicin treatment significantly decreased markers of oxidative stress, namely, protein oxidization and lipid peroxidization. However, behavior was not assessed in this study. Prior intracerebroventricular treatment with the antioxidant zinc sulfate (ZnSO4) prevented short-term memory impairments induced by systemic carmustine (BCNU) treatment. Specifically, BCNU treatment caused rats to make more errors during learning and recall of the radial arm maze, whereas treatment with ZnSO4 prior to BCNU prevented these deficits in learning and memory. In addition, hippocampal cell death and inflammation induced by BCNU treatment were prevented in rats pretreated with ZnSO4. Another case for reduction of anticancer drug-caused cognitive deficit with antioxidant is that there was no short-term memory impairment when rats that received cyclophosphamide and doxorubicin were treated with the antioxidant N-acetyl cysteine during chemotherapy. A recent review of 29 placebo-controlled randomized control trials of cancer survivors with deficits confirmed, by comparing psychometric tests, that the greatest benefits of *Ginkgo biloba* were found in executive functioning, selective attention, and memory.

Taken together, this information suggests that treatment with antioxidants prior to and during chemotherapy prevents the occurrence of cognitive deficits shortly after chemotherapy. Human trials of antioxidant supplementation in patients with breast and lung cancer have demonstrated an increase in survival, although alkylating agents, antitumor antibiotics, and topisomerase II inhibitors depend on the generation of free radicals for their therapeutic action. It was found, by investigating the MEDLINE® and CANCER-LIT® databases from 1965 to November 2003, that antioxidants and other nutrients do not interfere with chemotherapy of alkylating agents (e.g. cisplatin), antitumor antibiotics (e.g. doxorubicin) and topoisomerase II inhibitor (e.g. etoposide) or radiation therapy and can increase kill and increase survival.

As there are no proven treatments, there is a need for methods to properly treat chemotherapy-induced cognitive impairment. The present invention provides just such a method.

SUMMARY OF THE INVENTION

The present invention is directed to a method of treating chemotherapy-induced cognitive impairment.

One embodiment of the present invention is directed to a method of treating chemotherapy-induced cognitive impairment by administering to a patient in need at least one thiosemicarbazone compound.

Another embodiment of the present invention is directed to a method of treating chemotherapy-induced cognitive impairment by administering to a patient in need a composition comprising 3-aminopyridine-2-carboxaldehyde thiosemicarbazone, or a prodrug thereof.

Another embodiment of the present invention is directed to a method of treating chemotherapy-induced cognitive impairment by administering to a patient in need a composition comprising 3-aminopyridine-2-carboxaldehyde thiosemicarbazone the step of administering is intravenous, intraperitoneal, subcutaneous, intramuscular, topical, transdermal or oral.

The present invention further encompasses methods of treating chemotherapy-induced cognitive impairment by administering a composition comprising a compound of Formula I, or an analogue thereof:

Wherein R, $R_1$, $R_2$, $R_3$, and $R_4$ are independently selected from the group consisting of hydrogen, C1-8alkyl, C2-8alkenyl, C2-8alkynyl, C3-8cycloalkyl, C1-8haloalkyl, C6-10aryl, amino-C1-8alkyl, hydroxy-C1-8alkyl, C1-8alkoxye-C1-8alkyl, and C1-8alkanoyl, or $NR_1R_2$ taken in combination form a 3 to 7 member ring which may comprise 0, 1, or 2 additional ring heteroatoms selected from N, O, and S; $R_6$ is hydrogen, hydroxy, amino, or C1-8alkyl; $R_5$ and $R_7$ are independently selected from the group consisting of hydrogen, halide, hydroxy, thiol, amino, hydroxyamino, mono-C1-8alkylamino, di(C1-8alkyl)amino, C1-8alkoxy, C1-8alkyl, C1-8alkenyl, and C2-8alkynyl.

The present invention further encompasses methods of treating chemotherapy-induced cognitive impairment by administering a composition comprising a compound of Formula II, or an analogue thereof:

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implemented in other systems, and that any such variation would be within such modifications that do not part from the scope of the present invention. Before explaining the disclosed embodiments of the present invention in detail, it is to be understood that the invention is not limited in its application to the details of any particular arrangement shown, since the invention is capable of other embodiments. The terminology used herein is for the purpose of description and not of limitation. Further, although certain methods are described with reference to certain steps that are presented herein in certain order, in many instances, these steps may be performed in any order as would be appreciated by one skilled in the art, and the methods are not limited to the particular arrangement of steps disclosed herein.

The present invention is direct to method for the treatment of chemotherapy induced cognitive impairment comprising the step of administering to a patient a composition comprising a thiosemicarbazone compound. The means for synthesis of thiosemicarbazone compounds useful in the methods of the invention are well known in the art. Such synthetic schemes are described in U.S. Pat. Nos. 5,281,715; 5,767,134; 4,447,427; 5,869,676 and 5,721,259; all of which are incorporated herein by reference in their entirety.

The chemical structures of PAN-811's analogues are shown in U.S. Pat. No. 7,456,179, and patent applications of 20090275587, 20060194810 and 20060160826 each of which are hereby incorporated by reference.

The pharmaceutical compositions required by the present invention typically comprise a compound useful in the methods of the invention and a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Depending on the route of administration, the compound may be coated in a material to protect it from the action of enzymes, acids and other natural conditions which may inactivate the agent. For example, the compound can be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluoro-phosphate (DEP) and trasylol. Liposomes include water-in-oil-in-water emulsions as well as conventional liposomes. Dispersions can also be prepared in glycerol, liquid polyethylene glycols, and mixtures thereof and in oils. Under ordinary conditions of storage and use, these preparations may contain a preservative to prevent the growth of microorganisms.

The active agent in the composition (i.e., one or more thiosemicarbazones) preferably is formulated in the composition in a therapeutically effective amount. A "therapeutically effective amount" refers to an amount effective, at dosages and for periods of time necessary, to achieve the desired therapeutic result to thereby influence the therapeutic course of a particular disease state. A therapeutically effective amount of an active agent may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects. In another embodiment, the active agent is formulated in the composition in a prophylactically effective amount. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

A compound of the invention can be formulated into a pharmaceutical composition wherein the compound is the only active agent therein. Alternatively, the pharmaceutical composition can contain additional active agents. For example, two or more compounds of the invention may be used in combination.

3-aminopyridine-2-carboxaldehyde thiosemicarbazone (hereinafter "PAN-811"), with a molecular weight of 195.24 Da, has demonstrated potent neuroprotective activities in several neurodegenerative models. PAN-811 was originally developed for cancer therapy due to its ability to inhibit ribonucleotide reductase, a key enzyme required for DNA synthesis. Our previous studies demonstrated that PAN-811 at concentration of 0.45 µM fully blocked ischemic neurodegeneration and at 1.2 µM completely halted hypoxia-induced neuronal cell death (Jiang et al., 2006). PAN-811 was administered intracerebroventricularly (i.c.v.) at a dose of 50 µg per rat at 1 h after arterial occlusion. Staining of consecutive brain sections and computer-assisted quantitative analysis demonstrated that PAN-811 reduced the infarct volume by 59% in PAN-811 treated rats. We also investigated the effect of a single intravenous (i.v.) bolus injection of PAN-811. Two-hour MCAo with cerebral blood flow reduction of 75% or greater resulted in infarct formation, brain edema and a significant number of premature deaths. PAN-811 treatment reduced infarct volume in a dose dependent manner with a maximal protection of 50% at a dose of 2 mg/kg. PAN-811 treatment (2 mg/kg) also resulted in a 70% reduction in brain edema volume. Accordingly, the mortality in PAN-811 treated groups was collectively reduced by 44% (Jiang et al., 2008). Mechanistically PAN-811 not only prevents glutamate-induced excitatory cytotoxicity, veratridine-induced a sodium channel opening that is related to $Ca^{2+}$ influx and staurosporine-induced apoptosis, but also blocks oxidative stress-induced neuronal cell death in many ways. PAN-811 at a concentration as low as 1 µM suppressed in vitro hydrogen peroxide-induced LDH release by 78% (with P<0.01, compared to untreated/$H_2O_2$-insulted group) and at a concentration of 10 µM achieved maximal protection (by 90% comparing with untreated and $H_2O_2$-insulted group) with an $EC_{50}$ of –0.55 µM (Pan et al., 2009). PAN-811 also inhibited oxidative stress-induced cell death of human Alzheimer's disease-derived and age-matched olfactory neuroepithelial cells via suppression of intracellular reactive oxygen species. Importantly, PAN-811 manifested as a free radical scavenger in a cell free system where PAN-811 reduced 500 µM of a stable free radical diphenylpicrylhydrazyl by 70%. Taken together, PAN-811 has manifested as a potent antioxidant and neuroprotectant.

Based on the key role of oxidative stress in chemo brain and also the potent antioxidative and neuroprotective effects of PAN-811, we have discovered that PAN-811 is a therapeutic agent for chemotherapy-induced cognitive deficit or chemo brain. PAN-811 should inhibit chemotherapy-induced cognitive deficit that is not only caused with antimetabolites (cytarabine, gludarabine, fluorouracil, mercaptopurine, methotrexate, thioguanine, gemcitabine, hydroxyurea), mitotic inhibitors (vincristine, vinblastine, vinorelbine), topoisomerase inhibitors (topotecan, irenotecan), paclitaxel, docetaxel and asparaginase, but also with alkylating agents (busulfan, carmustine, lomustine, chlorambucil, cyclophosphamide, cisplatin, carboplatin, ifosamide, mechlorethamine, melphalan, thiotepa, dacarbazine, procarbazine), antitumor antibiotics (bleomycin, dactinomycin, daunorubicin, doxorubicin, idarubicin, mitomycin, mitoxantrone, plicamycin), topoisomerase II inhibitor (etoposide, teniposide), and radiation therapy.

Example 1

Materials and Methods

Neuronal Cell Culture. Mixed cortical and striatal neurons from embryonic day 17 male Sprague-Dawley rats (tissue obtained from NIH) were seeded into poly-D-lysine coated 96-well plates at density of 50,000 cells/well and initially cultured at 37° C., 5% CO2, in neurobasal medium (NB) with B27 supplement (Invitrogen) containing full strength of AOs to obtain highly enriched (95%) neurons. Since AOs, including vitamin E, vitamin E acetate, superoxide dismutase (SOD), catalase (CAT), and GSH, are additives to culture medium, reduction of AO concentration in culture medium provides an approach to determine the level of OS involvement in a neurotoxic process. In our study, the culture medium was replaced at a 50% ratio with NB plus B27 minus AOs twice at days 7 and 9 to set AO concentrations as 50% and 25%, respectively. At 16 days in vitro (d.i.v.), a fraction of the culture medium was harvested for lactate dehydrogenase (LDH) assay, and then AO concentration was reduced to 12.5% and cultured for a further 5 hours prior to ending the experiment.

Cancer Cell Culture. The mouse liver cancer cell line BNLT3 (gift of Dr. Jack Wands, Brown University) and the human lung cancer cell line H460 (ATCC) were seeded into 96-well plates at a density of 4,000 cells/well and cultured at 37° C., 5% CO2, in DMEM (11965, Gibco) supplemented with 10% fetal bovine serum, 20 mM HEPES, 1 mM sodium pyruvate, and 24 ng/mL gentamycin (all reagents came from Gibco).

Cell Insults and Treatments. Determination of concentration for each anticancer drug in our experiments was based on its reported concentration in human cerebral spinal fluid (CSF) in chemotherapy, literature report of its neurotoxicity in culture, and our preliminary in vitro experimental data. At 13 d.i.v., the neuronal cell cultures were insulted with 100 μM of MTX (M9929, Sigma), 25 μM of 5-FU (F6627, Sigma), or 3.5 μM of CDDP (sc-200896, Santa Cruz) for 3 days in absence or presence of PAN 811.Cl.H2O. For ROS examination, the neurons were insulted with both 100 μM of MTX and 25 μM of 5-FU by 15 d.i.v. PAN-811.Cl.H$_2$O was added to cultures to final concentrations of 1.25, 2.5, 5, and 10 μM at the same time as addition of the anticancer drugs. For cancer cell lines, the cells were insulted by the second day of cell seeding with the same concentration of MTX, 5-FU, or CDDP as used in neuronal culture in the absence or presence of 10 μM PAN-811.Cl.H2O for another 3 days.

Quantitative Assays and Morphological Assessment. Cell membrane integrity and mitochondrial function of either neurons or cancer cells were measured with LDH and 3-(4,5-dimethylthiazol-2-yl)-5-(3-carboxymethoxyphenyl)-2-(4-sulfophenyl)-2H-tetrazolium [MTS] analyses, respectively. The latter has been used to quantify cell survival. For the LDH assay, a mixture of a 35 μL aliquot of culture supernatant and 17.5 μL of Mixed Substrate, Enzyme and Dye Solutions (Sigma) was incubated at room temperature (RT) for 30 minutes. For the MTS assay, 10 μL of MTS reagent (Promega) was added to a culture well containing neurons in 50 μL of medium. The preparations were incubated at 37° C. for 2 hours. The preparations for both assays were then spectrophotometrically measured at 490 nm using a 96-well plate reader (Mode 550, Bio-Rad). Neuronal cell death was morphologically determined based on the integrity of the cell soma and continuity of neuronal processes. The change in number of cancer cells was judged directly by cell density. Cells were photographed under an inverted phase contrast microscope (IX 70, Olympus) using 10× or 20× objective.

ROS Examination. Neurons were incubated in 15 μM dihydrorhodamine 123 (DHR 123, Molecular Probes) for 30 min at 37° C. to determine intramitochondrial ROS levels. Fluorescence was photographed by using a fluorescentmicroscope and quantified by excitation at 485 nm and emission at 520 nm using a 96-well plate reader (Model 550, Bio-Rad).

Data Analysis. Data were generated from 4-6 replicate wells, expressed as mean±standard deviation (SD), and statistically evaluated at a significance level of 1% with one factor ANOVA or Student's t-test by using software VASSARSTATS (http://vassarstats.net/) followed by the Tukey HSD test. Figure symbols are as follows: #, $P<0.05$, and ##, $P<0.01$, compared with control; *, $P<0.05$, and **, $P<0.01$, compared with the insulted group; §§, $P<0.01$, compared with PAN-811 treated group by Student's t-test.

Results

Figure 1:
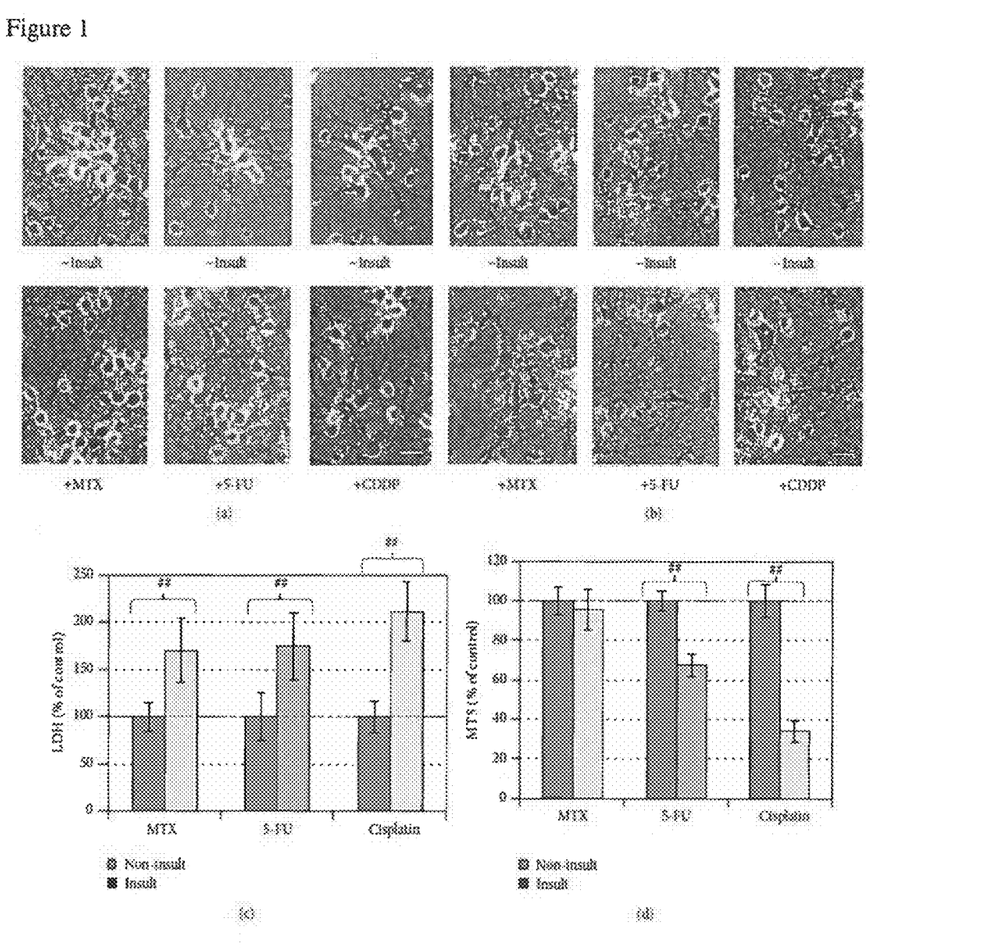
FIG. 1: Neurotoxicity of MTX, 5-FU, or CDDP in an AO-dependent manner. (a, b) Phase contrast photographs for neurons in 25% AO and 12.5% AO, respectively (bar=25 μm). (c) Cell membrane leakage was determined via the LDH analysis at the end of experiment for neurons in 25% AO (n=5). (d) Cell viability was determined with MTS analysis for neurons in 12.5% AO (n=5). The bar in green and bars in other colors indicate the cultures without an insult and with anticancer drug insults, respectively. LDH and MTS data are expressed as % of noninsulted control. Figure symbol is ##, $P<0.01$, compared with noninsult control group by Student's t-test.

MTX, 5-FU, or CDDP Elicited Neurotoxicity in an AOs—Dependent Manner. By 3 days following the insults, neither MTX at 100 μM, 5-FU at 25 μM, nor CDDP at 3.5 μM caused morphological changes, LDH release, or MTS reduction when neurons were cultured in the medium containing 100% or 50% AOs (data not shown). However, MTX, 5-FU, or CDDP at the same concentrations elicited significant LDH increase (indicating cell membrane leakage, FIG. 1(c)) in the culture supernatant when the AO concentration was reduced to 25%, although no cell damage was visible (FIG. 1(a)), and no change in MTS level was detectable (data not shown) under these conditions. When the AO concentration was reduced to 12.5% for 5 hours at 16 d.i.v., extensive neuronal cell death occurred in the cultures insulted with 25 μM 5-FU or 3.5 μM CDDP, as indicated by loss of cell bodies, together with interruption of neurite networks on the background (FIG. 1(b)). Corresponding to the morphological cell death, the MTS readings for 5-FU- and CDDP-insulted groups were reduced by 27% and 66%, respectively (FIG. 1(d)). MTX at 100 μM did not elicit significant MTS reduction (FIG. 1(d)) under 12.5% AO condition. Thus, the neurotoxicities elicited with MTX, 5-FU, or CDDP were dependent on AO reduction.

Figure 2:
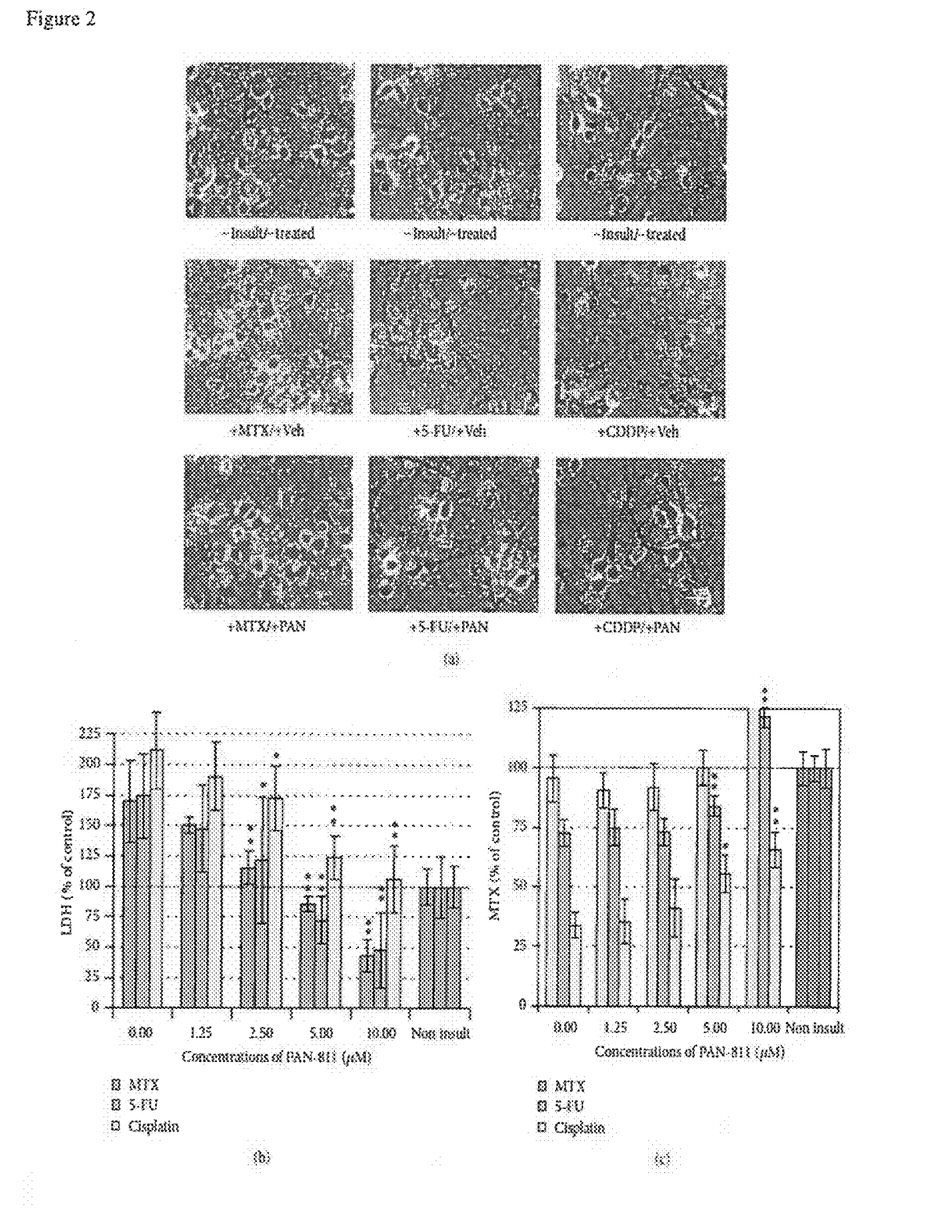
FIG. 2: Dose-dependent neuroprotection of PAN-811.Cl.$H_2O$ against anticancer drug-induced neurotoxicity. (a) Phase contrast photographs for neurons in 12.5% AO (bar=25 μm; PAN: PAN-811.Cl.$H_2O$). (b) LDH analysis for (a) (n=5). (c) MTS analysis for (a) (n=6). The bar in green and bars in other colors in the graphs indicate the cultures without an insult and with anticancer drug insults, respectively. Data are expressed as % of noninsulted control. Figure symbols are *, $P<0.05$, and **, $P<0.01$, compared with insult group alone (without PAN-811 treatment) by one-factor ANOVA followed with Tukey HSD test.

PAN-811 Dose-Dependently Suppresses MTX-, 5-FU-, or CDDP-Induced Neurotoxicity. We then examined PAN-811 for its effect on the anticancer drug-induced neurotoxicity at the 12.5% AO condition. MTX at 100 μM did not result in significant loss of cell number, while 5-FU at 25 μM or CDDP at 3.5 μM caused robust loss of neurons in culture (FIG. 2(a)). Correspondingly, MTX insult did not significantly affect the MTS reading, while 5-FU- and CDDP insulted cultures showed significant reduction in MTS readings (FIG. 2(c)). PAN-811 dose-dependently inhibited 5-FU- or CDDP-induced MTS reduction. PAN-811 at 10 μM completely blocked 5-FU-induced MTS reduction and inhibited CDDP-induced MTS reduction by 48%. The LDH release assay demonstrated that each of MTX at 100 μM, 5-FU at 25 μM, and CDDP at 3.5 μM resulted in significant increases in LDH reading (FIG. 2(b)). PAN-811 dose-dependently suppressed LDH increase caused by each anticancer drug. PAN-811 at 5 μM fully blocked LDH release in MTX-, 5-FU-, or CDDP-insulted cultures (with no statistically significant difference from untreated control culture by ANOVA analysis). Thus, PAN-811 was demonstrated as a potential neuroprotective compound for anticancer drug MTX-, 5-FU-, or CDDP-induced neurotoxicity.

Figure 3:
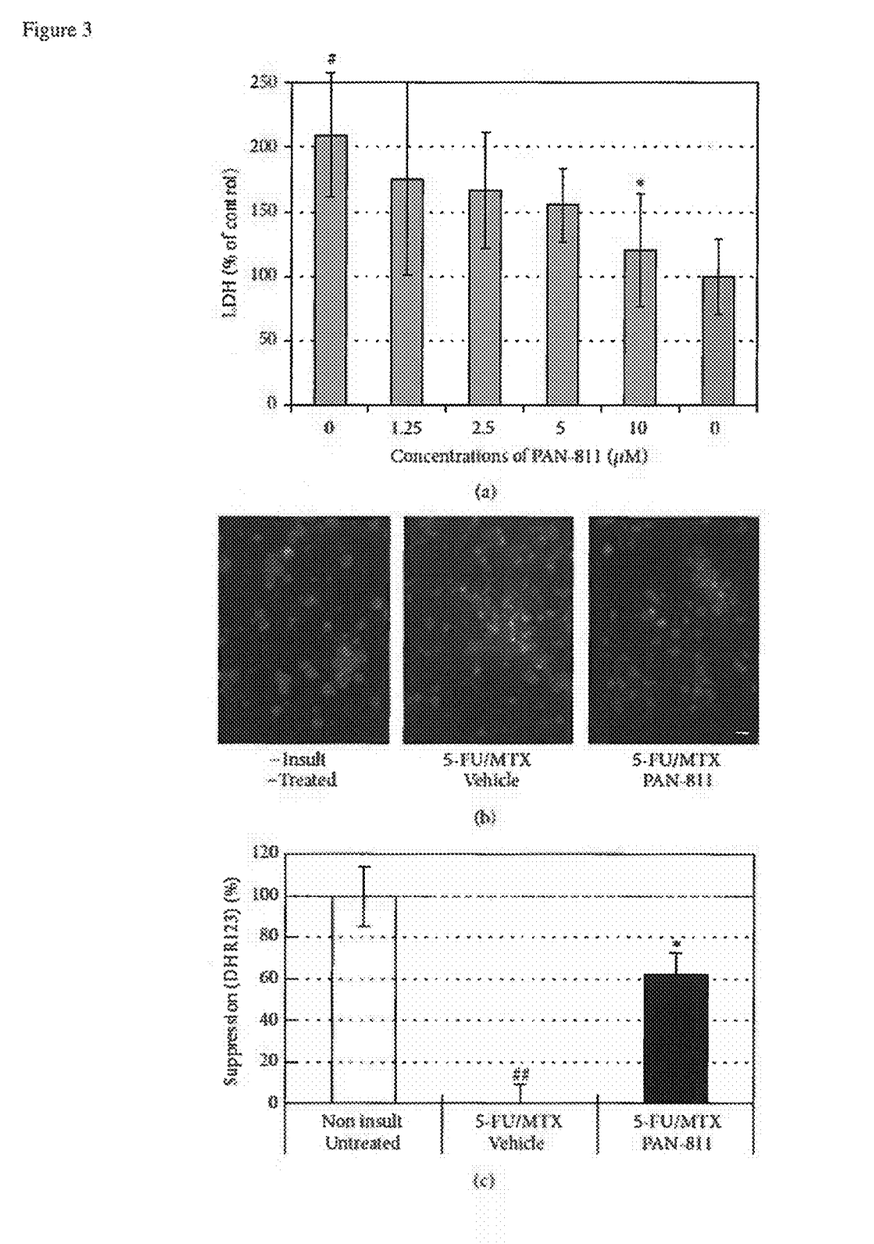
FIG. 3: Suppression of 5-FU/MTX-induced increases in LDH and DHR123 readings by PAN-811. (a) LDH release analysis for neurons that were cultured in 17.5% AOs containing medium and insulted with both 100 μMMTX and 25 μM 5-FU in the absence or presence of PAN-811.Cl.H$_2$O at different concentrations for 1 day (n=6). (b) Fluorescent microscope for neurons in 17.5% AOs-containing medium insulted with both 100 μMMTX and 25 μM 5-FU in the absence or presence of 10 μM PAN-811.Cl.H$_2$O for 1 day and incubated with DHR123 for 30 min (bar=50 μm). (c) Quantification of (b) at excitation at 485 nm and emission at 520 nm (n=4). Data are expressed as % suppression= [(Insulted&Untreated−Insulted&Treated)/ (Insulted&Untreated−Nonlnsulted&Untreated)*100%]. Figure symbols are *, P<0.05, compared with insult group alone (without PAN-811 treatment) by Student's t-test (one tail) and one-factor ANOVA followed by Tukey HSD test; #, P<0.05; ##, P<0.01, compared with noninsult/untreated control group by one-factor ANOVA followed with Tukey HSD test.

PAN-811 Suppresses Cell Membrane Leakage When MTX and 5-FU Are Coadministered. Since MTX and 5-FU are coadministered for cancer therapies in many cases, we were interested to know if PAN-811 can block neurotoxicity that is elicited with a combined insult with both MTX and 5-FU. An insult with a combined 100 μM MTX and 25 μM 5-FU resulted in a 109% increase in LDH reading by comparison with noninsulted control group (P<0.05 by ANOVA; FIG. 3(a)). PAN-811 showed concentration-dependent suppression of LDH release within the tested range from 1.25 to 10 μM. PAN-811 at 10 μM fully inhibited MTX/5-FU-elicited LDH increase.

PAN-811 Inhibits MTX- and 5-FU-Elicited OS. To understand the underlying mechanism for MTX- and 5-Fu induced neurotoxicity, a cell-permeable fluorogenic probe DHR 123 was used for the detection of intramitochondrial ROS. Neuronal insult with coadministered 100 μM MTX and 25 μM 5-FU greatly increased intensity of DHR 124 fluorescence (FIG. 3(b)), resulting in a 33.4% increase in DHR123 level in comparison with noninsulted group (P<0.05 by t-test, data not shown). PAN-811 at 10 μM provided significant suppression to the increased ROS, showing a 62.3% suppression rate (FIG. 3(c)).

Figure 4:
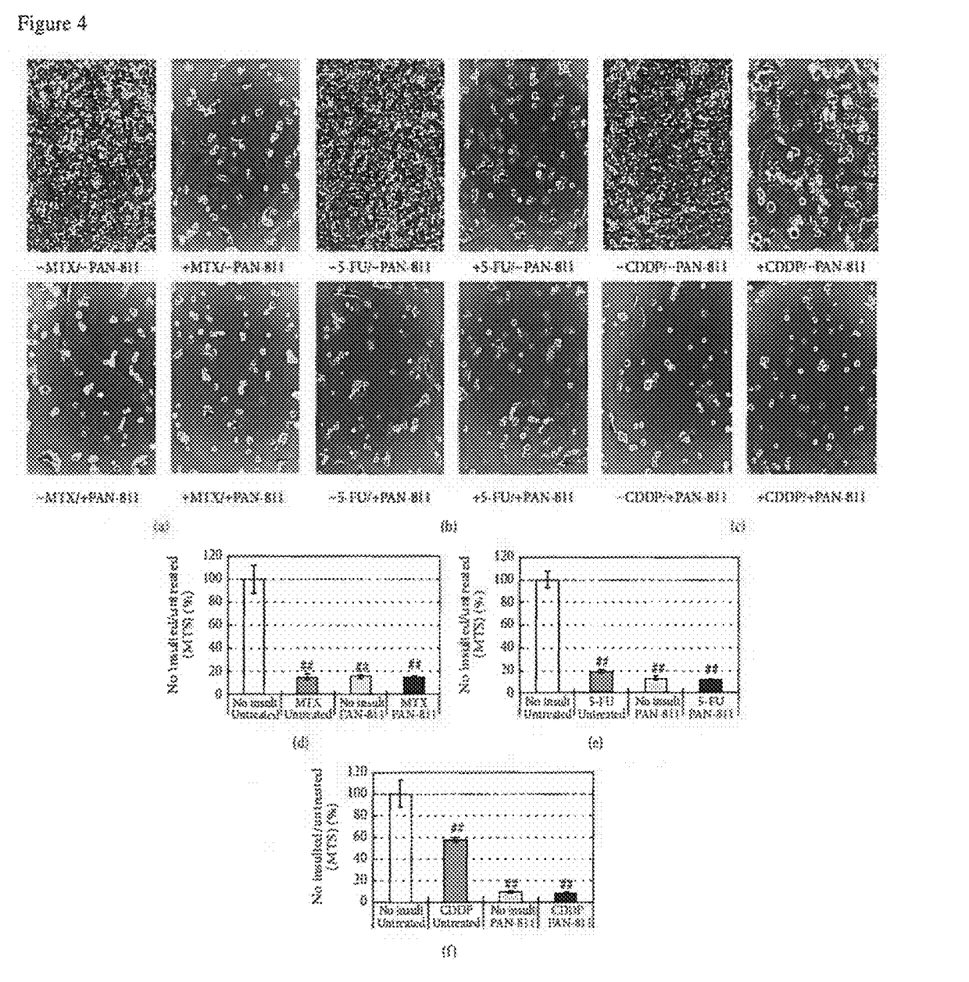
FIG. 4: No interference of PAN-811.Cl.H$_2$O with anticancer drug-induced cytotoxicity to mouse cancer cell line BNLT3. (a)-(c) Phase contrast photographs for BNLT3 cells that were treated without or with 10 μMPAN-811.Cl.H$_2$O and insulted with 100 μMMTX, 25 μM5-FU, and 3.5 μM CDDP for 3 days, respectively (bar=50 μm). (d)-(f) MTX analysis corresponding to (a)-(c) (n=6). Data are expressed as % of noninsulted/untreated control. Figure symbol is ##, P<0.01, compared with noninsult/untreated control group by one-factor ANOVA followed with Tukey HSD test.

PAN-811 Shows No Antagonistic Effect on MTX-, 5-FU-, or CDDP-Induced Cytotoxicity in BNLT3 Cells. To understand whether PAN-811 could interfere with anticancer efficacy of tested anticancer drugs, the mouse liver cancer cell line BNLT3 was cotreated with each anticancer drug at the concentrations used for elicitation of neurotoxicity and 10 μM PAN-811, the highest concentration used for neuronal protection in these experiments. A 3-day insult with 100 μM MTX severely reduced the cancer cell number (FIG. 4(a)). In the culture treated with 10 μM PAN-811 alone or cotreated with 100 μM MTX and 10 μM PAN-811, cell density was also much lower than that in no-insult control. Quantitatively, MTX at 100 μM reduced MTS reading by 85% (FIG. 4(d)), while PAN-811 at 10 μM reduced MTS reading to the same level as MTX. A cotreatment with both did not cause any further reduction in MTS reading when comparing with MTX alone. Similarly, 5-FU at 25 μM significantly reduced the cell density of the cancer cells, and a cotreatment with both 25 μM 5-FU and 10 μM PAN-811 significantly decreased the cell number as well (FIG. 4(b)). Quantitatively, 5-FU at 25 μM reduced MTS reading by 84%, which was less efficient than 10 μM PAN-811 group (FIG. 4(e)). A cotreatment with both caused a further reduction in MTS reading when comparing with 5-FU alone. No synergistic effect between 5-FU and PAN-811 could be detected. An insult with 3.5 μM CDDP also caused a decrease in the cell density (FIG. 4(c)), while a treatment with PAN-811 alone or a cotreatment with both 3.5 μM CDDP and 10 μM PAN-811 introduced a significant reduction in the cell density. Quantitatively, 3.5 μM CDDP reduced MTS reading by 44%, while 10 μMPAN-811 caused a 94% reduction in MTS reading (FIG. 4(f)). A cotreatment with both did not introduce an extra reduction in MTS reading by comparing with PAN-811 alone, despite showing much lower reading than CDDP alone (P<0.01). In general, PAN-811 did not show any inhibition in the effect of MTX, 5-FU, or CDDP on BNLT3 cells, neither did it demonstrate any synergistic effect with each tested anticancer drug on BNLT3 cell growth.

Figure 5:
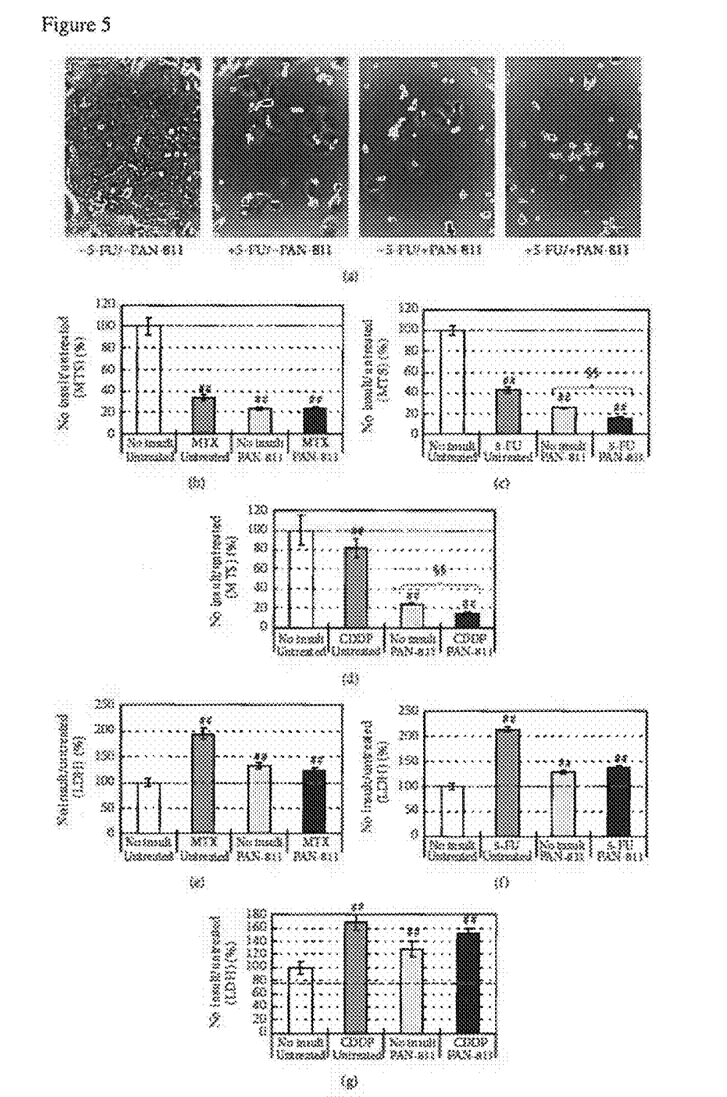
FIG. 5: Effects of PAN-811.Cl.H$_2$O on anticancer drug-induced cytotoxicities to human cancer cell H460. (a) Phase contrast photographs for the H460 cells that received 25 μM 5-FU, 10 μM PAN-811, or both for 3 days (bar=50 μm). (b)-(d) MTS analysis for the H460 cells that received 10 μM PAN-811.Cl.H2O, one of 100 μM MTX, 25 μM 5-FU, and 3.5 μM CDDP, or both 10 μM PAN-811.Cl.H$_2$O and one of these anticancer drugs for 3 days, respectively (n=6). (e)-(g) LDH analysis for (b)-(d) (n=6). Data are expressed as % of noninsulted/untreated control. Figure symbol is ##, P<0.01, compared with noninsult/untreated control group by one-factor ANOVA followed with Tukey HSD test.

PAN-811 Shows No Antagonistic Effect on MTX-, 5-FU-, or CDDP-Induced Cell Death of H460 Cells, While Demonstrating a Synergistic Effect with 5-FU or CDDP on Suppression of the Cell Growth. To understand whether there is any negative effect of PAN-811 on the efficacy of tested anticancer drugs in humans, the human lung cancer cell line H460 was treated with each of these anticancer drugs at the concentrations used for elicitation of neurotoxicity, in the absence or presence of 10 μM PAN-811. A3-day insult with 100 μMMTX, 10 μMPAN-811, or both robustly decreased the cell density of H460 in culture (data not shown). Quantitatively, 100 μM MTX and 10 μM PAN-811 reduced MTS readings by 67% and 76%, respectively. The MTS reading for a cotreatment with both 100 μMMTX and 10 μM PAN-811 was about the same as 10 μM PAN-811 alone (FIG. 5(b)). In membrane integrity analysis (FIG. 5(e)), 100 μM MTX resulted in a 95% increase in LDH reading in the culture supernatant, while 10 μM PAN-811 led to a 31% increase in the LDH reading. A cotreatment with 100 μM MTX and 10 μM PAN-811 reduced LDH reading by 70% when compared with MTX group (P<0.01 by ANOVA), indicating an inhibitory effect of PAN-811 on MTX-caused membrane leakage. Similarly, a 3-day treatment with 25 μM 5-FU, 10 μM PAN-811, or both robustly decreased the cell density of H460 in culture (FIG. 5(a)). Quantitatively, 25 μM 5-FU and 10 μM PAN-811 reduced MTS readings by 57% and 74%, respectively (FIG. 5(c)). In contrast, a cotreatment with 25 μM 5-FU and 10 μM PAN-811 reduced MTS readings by 84%, which shows a statistically significant difference from 5-FU (P<0.01) or PAN-811 alone (P<0.01), indicating a synergistic effect of 5-FU and PAN-811 on suppression of growth of human lung cancer cell H460. In membrane integrity analysis (FIG. 5(f)), 25 μM5-FU resulted in a 124% increase in LDH reading in the culture supernatant, while 10 μM PAN-811 led to a 30% increase in the LDH reading. A cotreatment with 100 μM5-FU and 100 μMPAN-811 enhanced LDH reading by 40%, which is much lower than that in the group with 25 μM5-FU alone. It indicates an inhibitory effect of PAN-811 on 5-FU-caused membrane leakage. A 3-day treatment with 3.5 μM CDDP, 10 μM PAN-811, or both greatly decreased the cell density of H460 in culture. Quantitatively, 3.5 μM CDDP and 10 μM PAN-811 reduced MTS readings by 22% and 75%, respectively (FIG. 5(d)). A cotreatment with 3.5 μM CDDP and 10 μM PAN-811 reduced MTS readings by 85%, which shows a statistically significant difference from CDDP (P<0.01 by ANOVA) or PAN-811 alone (P<0.01 by t-test), indicating a synergistic effect of CDDP and PAN-811 on suppression of growth of human lung cancer cell H460. In membrane integrity analysis (FIG. 5(g)), 3.5 μM CDDP resulted in a 71% increase in LDH reading in the culture supernatant, while 10 μM PAN-811 led to a 30% increase in the LDH reading. A cotreatment with 3.5 μM CDDP and 10 μMPAN-811 enhanced LDH reading by 57%, which is a statistically significant difference from that in the group with 3.5 μM CDDP alone (P<0.01), demonstrating an inhibitory effect of PAN-811 on CDDP-induced membrane leakage. In general, PAN-811 did not show any inhibition in the effect of MTX, 5-FU, or CDDP on cell growth of H460 cells, although it manifested an inhibitory effect on MTX-, 5-FU-, or CDDP-induced membrane leakage. A synergistic effect between 5-FU and PAN-811 or between CDDP and PAN-811 occurred on suppression of H460 cell survival.

While the invention has been described with reference to certain exemplary embodiments thereof, those skilled in the art may make various modifications to the described embodiments of the invention without departing from the scope of the invention. The terms and descriptions used herein are set forth by way of illustration only and not meant as limitations. In particular, although the present invention has been described by way of examples, a variety of compositions and processes would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A method of treating a person having chemotherapy induced cognitive impairment caused as a side-effect of an anticancer drug comprising (i) administering to said person an effective amount of a neuroprotective compound of 3-aminopyridine-2-carboxyaldehyde thiosemicarbazone that results in a lessening of the chemotherapy induced cognitive impairment.

2. The method of claim 1, wherein the anticancer drug is 5-FU.

3. The method of claim 1, wherein the anticancer drug is MTH.

4. The method of claim 1, wherein the anticancer drug is CDDP.

5. The method of claim 1, wherein the step of administering is intravenous, intraperitoneal, subcutaneous, intramuscular, topical, transdermal or oral.

6. The method of claim 1, wherein the compound is contained in an injectable and/or infusible solution.

7. The method of claim 1, wherein the compound is formulated as a micro emulsion.

8. The method of claim 1, wherein the compound is formulated as a liposome.

9. A method for the treatment of chemotherapy induced cognitive impairment resulting from the administration of an anticancer drug comprising:
    (i) administering to a patient experiencing chemotherapy induced cognitive impairment an effective amount of a neuroprotective compound of 3-aminopyridine-2-carboxyaldehyde thiosemicarbazone; and
    (ii) administering to said patient an anticancer drug;
wherein the administration of the neuroprotective compound does not inhibit the efficiency of the anticancer drug.

10. The method of claim 9, wherein the anticancer drug is 5-FU.

11. The method of claim 9, wherein the anticancer drug is MTH.

12. The method of claim 9, wherein the anticancer drug is CDDP.

13. A method for the treatment of chemotherapy-induced cognitive impairment caused by the administration of an anticancer drug comprising (i) administering to a patient experiencing chemotherapy induced cognitive impairment, a neuroprotective composition comprising at least one thiosemicarbazone compound or an analogue thereof:

that results in a reduction of the chemotherapy induced cognitive impairment.

14. A method for the treatment of chemotherapy induced cognitive impairment for a patient treated with an anticancer drug, comprising the steps of:
    (i) administering to a patient experiencing chemotherapy induced cognitive impairment a neuroprotective compound of 3-aminopyridine-2-carboxyaldehyde thiosemicarbazone to preserve cell neurons;
wherein the administration of the neuroprotective compound does not inhibit the efficiency of the anticancer drug.

15. The method of claim 14, wherein the anticancer drug is 5-FU.

16. The method of claim 14, wherein the anticancer drug is MTH.

17. The method of claim 14, wherein the anticancer drug is CDDP.

18. The method of claim 14, wherein the step of administering is intravenous, intraperitoneal, subcutaneous, intramuscular, topical, transdermal or oral.

19. The method of claim 14, wherein the compound is contained in an injectable and/or infusible solution.

20. The method of claim 14, wherein the compound is formulated as a micro emulsion.

21. The method of claim 14, wherein the compound is formulated as a liposome.

* * * * *